US009016283B2

(12) United States Patent
Paulussen et al.

(10) Patent No.: US 9,016,283 B2
(45) Date of Patent: Apr. 28, 2015

(54) BACKBOARD FOR AN AUTOMATED CPR SYSTEM

(75) Inventors: Igor Wilhelmus Franciscus Paulussen, Eindhoven (NL); Pierre Hermanus Woerlee, Eindhoven (NL); Gerrit Jan Noordergraaf, Diessen (NL)

(73) Assignee: Koninklijke Philips N.V., Eindhoven (NL)

( * ) Notice: Subject to any disclaimer, the term of this patent is extended or adjusted under 35 U.S.C. 154(b) by 182 days.

(21) Appl. No.: 13/264,178

(22) PCT Filed: Apr. 14, 2010

(86) PCT No.: PCT/IB2010/051600

§ 371 (c)(1), (2), (4) Date: Oct. 13, 2011

(87) PCT Pub. No.: WO2010/119401

PCT Pub. Date: Oct. 21, 2010

(65) Prior Publication Data

US 2012/0042881 A1 Feb. 23, 2012

(30) Foreign Application Priority Data

Apr. 15, 2009 (EP) .................................... 09157987

(51) Int. Cl.

*A61F 5/37* (2006.01)
*A61H 31/00* (2006.01)

(52) U.S. Cl.

CPC .................................... *A61H 31/008* (2013.01)

(58) Field of Classification Search

USPC ................. 128/869–870, 876; 602/32; 5/601, 5/621–625, 628, 637, 652, 657

See application file for complete search history.

(56) References Cited

U.S. PATENT DOCUMENTS

| | | | | |
|---|---|---|---|---|
| 6,223,749 | B1 * | 5/2001 | Beaty | 128/869 |
| 6,371,119 | B1 * | 4/2002 | Zadini et al. | 128/845 |
| 7,063,461 | B2 * | 6/2006 | Coppens et al. | 378/208 |
| 2003/0181834 | A1 | 9/2003 | Sebelious et al. | |
| 2008/0097257 | A1 | 4/2008 | Stromsnes | |
| 2008/0142022 | A1 * | 6/2008 | Biondo et al. | 128/845 |

FOREIGN PATENT DOCUMENTS

| | | | |
|---|---|---|---|
| FR | 2286641 | A1 | 4/1976 |
| JP | 2008132312 | A | 6/2008 |
| WO | 0128484 | A1 | 4/2001 |

* cited by examiner

*Primary Examiner* — Michael A. Brown

(57) ABSTRACT

A backboard for an automated cardio pulmonary resuscitation system, said backboard comprising a board element, the board element defining a plane and having a top edge, a bottom edge a first side edge and a second side edge; a set of connectors adapted for connection of the backboard to an automated cardio pulmonary resuscitation unit, said connectors being provided at said side edges; and at least one set of stabilizing elements extending away from an edge and transversely to said plane.

13 Claims, 6 Drawing Sheets

BACKBOARD FOR AN AUTOMATED CPR SYSTEM

FIELD OF THE INVENTION

The present invention relates to a backboard suitable for use in an automated cardio pulmonary resuscitation (A-CPR) system. More particularly the invention relates to a backboard for supporting and stabilizing a patient while providing automated CPR of the type where a compression- and/or decompression- and/or respiratory unit is attachable to the backboard.

BACKGROUND OF THE INVENTION

Automated CPR systems are designed to execute cardio pulmonary resuscitation in an automated fashion, so to give a more reliable and sustainable resuscitation compared to a manual one. An A-CPR system typically comprises a backboard and a unit having a mechanical heart-stimulator, respiratory aid and possibly electrodes for electrical resuscitation. During use, a patient is placed on the backboard, back down, and an A-CPR-unit is attached to the backboard. When doing so it is important to transfer the force provided by mechanical heart-stimulator from the A-CPR-unit to the patient's sternum in a controlled but still forceful way. The force exerted on the patient's sternum will cause the patient to be moved relative to the backboard and the A-CPR-unit. This effect is highly undesirable because of the possible injuries that can arise from this A-CPR system's force-induced movement of the patient's sternum. Such injuries could be fractures of ribs, puncturing of the liver, puncturing of the lungs and/or other force trauma related injuries. In order to prevent injuries, the rescue personnel must spend a lot of time adjusting the position of the patient on the backboard. Naturally this is undesirable, since during resuscitation, accuracy and time are crucial.

US 2004/0230140 A1 discloses one such A-CPR-unit connectable to a backboard comprising a neck support being sufficiently high so the subject's head falls back and rests on a backplate while placing the subject's mouth in a suitable open position for unobstructed or clear access to the airways. This device suffers from the common problem with prior art backboards relating to positioning a patient correctly in a centered position relative to the automated cardio pulmonary resuscitation system (A-CPR) when in use. It has a long set-up time, and once the A-CPR unit is started and mechanical heart stimulation is initiated the patient may move relative to the backboard and the A-PCR system due to insufficient fixation and the forceful mechanical stimulation. Thus, in some case further time may be needed to reposition the patient with respect to the backboard and the A-PCR-unit.

Hence, an improved backboard would be advantageous, and in particular a backboard more stabilizing, more centered relative to the A-CPR unit and/or more reliable.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide a backboard that solves the above mentioned problems of the prior art with stabilizing the patient on a backboard relative to an automated cardio pulmonary resuscitation unit.

In an embodiment of the invention the backboard comprises a board element, the board element defining a plane and having a top edge, a bottom edge, a first side edge and a second side edge suitable for a variety of patients' body sizes. A set of connectors are provided at the first- and second side edges adapted for connection of the backboard to an automated cardio pulmonary resuscitation system. A set of shoulder stops formed as rigid arms are provided at the top edge of the board element and extending transversely to the plane defined by the board element aiding in the stabilization of the patient in a cranial-caudal direction.

In further embodiments, the shoulder stops may be adjustable in a direction parallel and/or perpendicular to the first- and second side edges. Thereby adjustment of the shoulder stops in one or two dimensions is enabled in order to fit a variety of patients' neck sizes and a variety of arm pit to shoulder-lengths. Thus further stabilization or fixation of the patient with respect the backboard and the A-PCR unit is accomplished.

The shoulder stops are in another embodiment formed integrated with the board element.

In either embodiment the shoulder stops may be formed as L-shaped or semicircular-shaped arms, thus providing good contact between the shoulder stops and the shoulders of the patient, and thereby further aiding in the stabilization of the patient on the backboard.

In further embodiments the board element of the backboard may be provided with a neck rest, formed at the top edge. The neck rest may be attachable/detachable or it may be formed integrated with the board element. The neck rest may be provided as an inflatable collar and/or pad(s) and/or cushion(s). The neck rest allows positioning the neck//throat/head in such a way that the airways are free and cleared for oxygenation by either mouth-to-mouth resuscitation or an oxygen mask. Further a neck rest may aid in positioning the neck at the shoulder stops, and thus stabilize the patient's position, and further prevent injuries of the patient caused by movement of the head. A detachable neck rest further allows for easy cleaning.

Additionally or alternatively, a shoulder stop padding may be formed on the inner sides of the shoulder stops. The padding may be in the form of an inflatable collar and/or pad(s) and/or cushion(s). The padding aids in positioning and fixating the neck of the patient against lateral movement with respect to the board element. Preferably, the shoulder stop padding is detachable from the shoulder stops in order to allow for thorough cleaning.

In further embodiments the board element of the backboard may additionally or alternatively be provided with a head rest. The head rest may be formed as an attachable/detachable plate and/or as a retractable plate. The head rest enables the head of the patient to be supported if the backboard needs to be lifted, by preventing the head to move with respect to the board element.

The board element, the shoulder stops and/or the head rest are preferably formed in a material transparent to radiation e.g. plastic used in scanning techniques such as x-ray. Thereby, the patient may be scanned while still positioned on the backboard, thus providing support for the patient.

In a further embodiment the board element of the backboard may comprise a second set of arms, the connectors for the automated cardio pulmonary resuscitation unit being provided on the second set of arms, the second set of arms being extendable from the board element in a direction perpendicular to the first- and second side edges and in a direction perpendicular to the plane defined by the board element. Thereby the connection point between the cardio pulmonary resuscitation unit and the backboard is moved upwards and outwards with respect to a patient placed on the backboard, and thus the cardio pulmonary resuscitation unit may more easily be connected to the backboard. This will facilitate a quick and precise and more gentle positioning of the cardio pulmonary resuscitation unit even when the patient is very large e.g. due to swelling or obesity. The connection of the cardio pulmonary resuscitation unit to the backboard is also facilitated because, it prevents loose parts of the patients clothes (which are cut open to allow access to the chest of the patient) from covering the connectors.

The extension of the second set of arms is preferably provided by sliding the second set of arms in chutes formed in the board element from a closed to an extended position. Alternatively the extension may be provided by a hinged mechanism rotating the second set of arms from a closed to an extended position. The second set of arms preferably comprises a locking mechanism for locking the arms in the closed- and/or extended position.

The second set of arms may be formed of plastic or they may be formed of a metal.

In an embodiment, the second set of arms may be detachable from the board element. Thereby, the second set of arms may be detached for easy cleaning of the board element and the second set of arms, these parts being exposed to various fluids, e.g. blood, during use.

Also, in embodiments, where the second set of arms is formed in metal, the detachment will allow the backboard to be used to support the patient during electromagnetic scanning.

In an embodiment the connectors are formed as rails. Thus, the automated cardio pulmonary resuscitation unit is enabled to be slideable for easy positioning of the automated cardio pulmonary resuscitation unit relative to the sternum. The rails are formed to allow sliding of the automated cardio pulmonary resuscitation unit in a direction parallel to the side edges of the board element.

In a further embodiment, the board element may comprise a set of handles, provided on the board element at the first and second side edge adjacent to the second set of arms opposite to the shoulder stops, enabling for easy handling of the backboard.

In a second aspect of the invention the objects may be achieved by an automated cardio pulmonary resuscitation system comprising a backboard according to any embodiments described above and an automated cardio pulmonary resuscitation unit.

The automated cardio pulmonary resuscitation unit preferably comprises a mechanical heart-stimulator and a respiratory aid.

BRIEF DESCRIPTION OF THE FIGURES

The present invention will now be explained, by way of example only, with reference to the accompanying Figures, where FIG. 1A, in a perspective view, shows a backboard according to an embodiment of the invention with a second set of arms in an extended position.

DETAILED DESCRIPTION OF AN EMBODIMENT

Figure 1A:
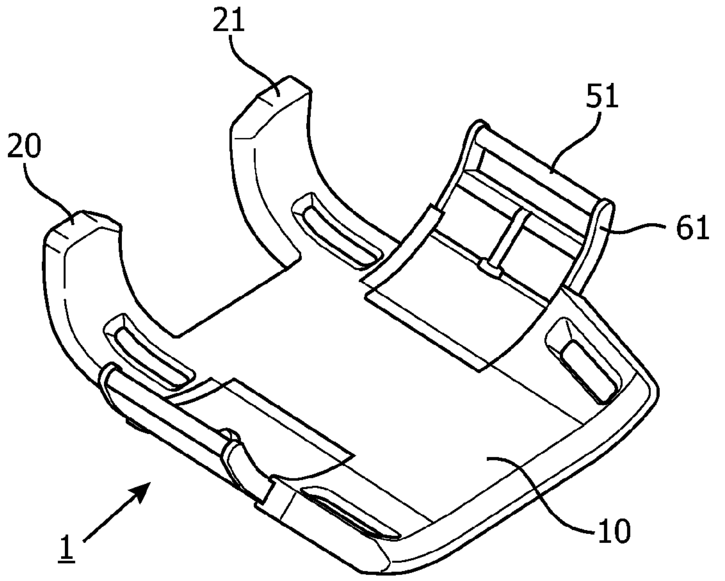
FIGS. 1B and 1C, in a sectional view and in a top view, respectively, shows the backboard of FIG. 1A.
Figure 1B:
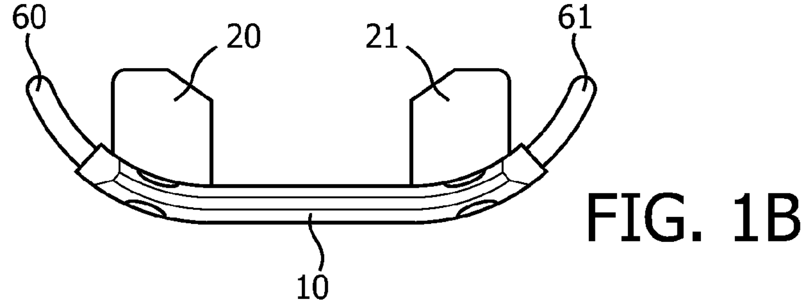
Figure 1C:
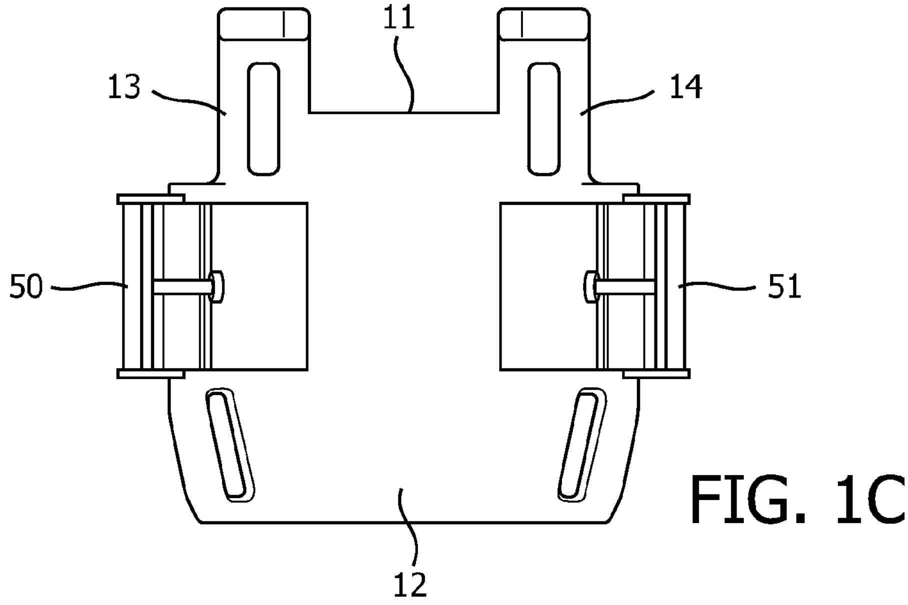

In FIGS. 1A-C a backboard 1, according to an embodiment of the invention, is shown. The backboard comprises a board element 10 and shoulder stops 20, 21. The board element 10 is substantially planar, and has a top and bottom surface 15, 16 (see FIG. 4). The top surface 15 provides a rest for the back of a patient. It may be entirely planar, or it may, as shown, be slightly concave to provide closer fit to the back of a patient. The board element 10 defines a plane, P. The board element 10 may be rectangular, and further comprises a top edge 11 and a bottom edge 12 and side edges 13, 14. In other embodiments (not shown) the board may have other shapes, e.g. oval.

The backboard 1 further comprises shoulder stops 20, 21. The shoulder stops 20, 21 is in one embodiment, as shown in FIG. 1, formed as an integrated part of the board element 10, i.e. the backboard is a one-part piece, formed e.g. by molding or other one-part piece techniques. In other embodiments (not shown), the board element 10 and shoulder stops 20, 21 form an assembly, where the shoulder stops 20, 21 may be connected to the board element 10 by screws, glue, welding or other connection techniques.

Shoulder stops 20, 21 are formed as rigid, or possibly, slightly flexible arms, such that they are able to sustain a patient on the backboard 1 when an A-CPR unit is operating and/or when the backboard 1 is lifted, tilted or otherways roughly handled during use.

The shoulder stops 20, 21 are provided at the top edge 11 of the board element 10 and extend parallel to the side edges 13, 14. A section of each arm forming the shoulder stops 20, 21 extend transversely to plane, P. Shoulder stops 20, 21 are preferably L-shaped as shown in FIGS. 1A-C or in other embodiments (not shown) semicirculary shaped or another form enabling a close fit between the shoulder stops 20, 21 and the patients shoulders.

The stabilization of a patient positioned on the backboard 10 is a crucial step in an A-CPR system because of the force the A-CPR-unit delivers to the patients sternum. It is realized that the force applied to the sternum moves the body in a predominately cranial direction, and relative to the A-CPR unit. This movement is produced by the force of the A-CPR units mechanical heart stimulator when pressing on the sternum. The rigid shoulder stops 20, 21 prevent this movement. In the prior art backboards having only a neck support, the modest height of the neck support will not prevent the patient from moving in a cranial direction due to the mechanical pounding by the A-CPR unit, and because the patient's clothes reduces friction between the backboard and the patient's body. Thus, there is a risk that the patient's body will slide over the neck support.

In another embodiment (not shown) of the backboard 1, the shoulder stops 20, 21 may be adjustably connected to the board element 10, such that the distance between the individual shoulder stops 20, 21, in a direction perpendicular to the side edges 13, 14, may be varied. Thereby, the backboard may be adapted for patients of variable neck and shoulder widths.

Additionally, or alternatively, the shoulder stops 20, 21 may be adjustable in a direction parallel to the side edges 13, 14, thereby enabling the backboard 1 to be adapted to patients with varying neck length and upper body sizes.

The shoulder stops' 20, 21 adjustability in a perpendicular and/or parallel direction to the side edges 13, 14 may be provided by a section of the arms forming the shoulder stops being guided in grooves, or channels formed in or on (the backside of) the board element 10 or in furnishings provided on the backside of the board element.

Figure 9:
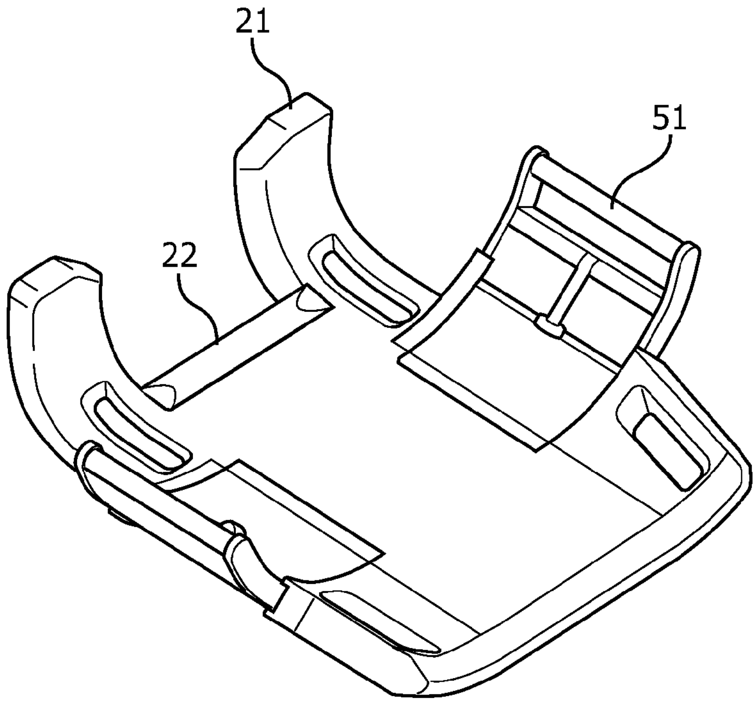
FIG. 9, in a perspective view, shows a backboard according to an embodiment of the invention, having a neck support.
Figure 10:
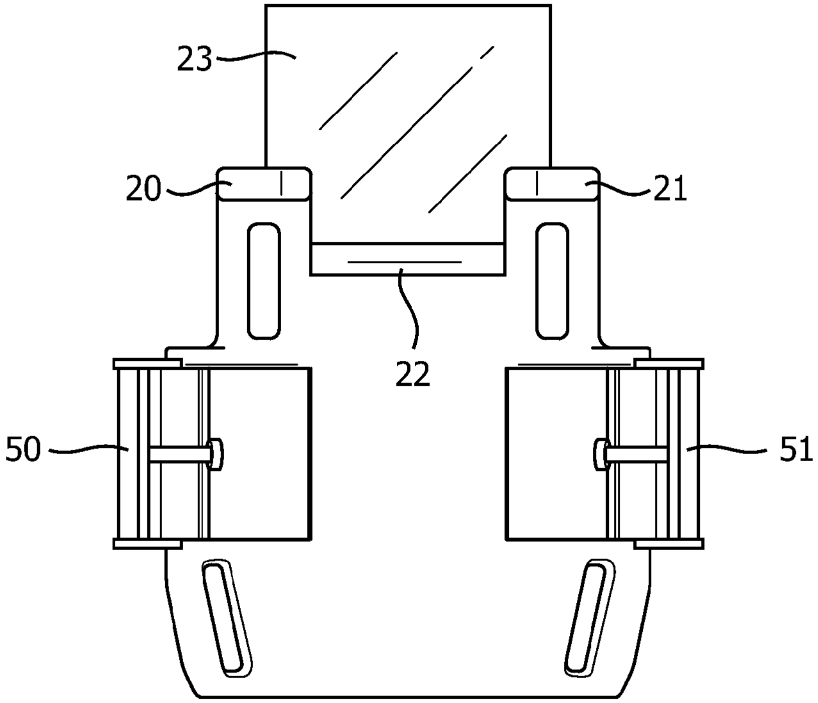
FIG. 10, in a perspective view, shows a backboard according to yet an embodiment of the invention, having with a neck- and a head support.

In further embodiments the backboard 1 may comprise a neck support 22, e.g. in the form of a collar and/or cushion(s) and/or pad(s) (see FIGS. 9 and 10), the neck support 22 being provided for aiding in the positioning of the patients head relative to the backboard 1 and/or for the comfortability of the patient. The neck support 22 is adapted to support and lift the neck to sustain the patients neck and head in a position providing clear airways for oxygenation and for avoiding obstruction of the airways of the patient.

The neck support 22 may be detachably attached on the board element 10 at the top edge 11 of the board element 10. The collar and/or cushion(s) and/or pad(s) forming the neck support 22 may be formed as inflatable part(s). Thereby, room for storage of the backboard, when not in use, may be minimized. Inflation of said neck supports could be provided by the use of oxygen from an oxygenation tank associated with the A-CPR unit or similar portable gas devices to provide automatic inflation. Alternatively, the collar and/or pad(s) and/or cushion(s) may be manually inflatable (by pump or oral inflation).

Additionally or alternatively, a padding in the form of pads or cushions may be formed on the shoulder stops 20, 21 on the side facing the patients neck, the padding providing comfort and sideways fixation of the neck/throat.

In a further embodiment (see FIG. 10), a head rest 23 is provided at the top edge 11 of the board element 10. Thereby the backboard 1 may be lifted and moved with the patient still being positioned on the backboard, and without the patients head tilting or changing position relative to the board element 10. Thereby, further injuries to the patient may be prevented.

The head rest 23 may be formed as an attachable/detachable plate, in order to save storage space, when the backboard is not in use. In further embodiments (not shown) the head rest may be extendable from the board element 10.

The board element 10 comprises a set of connectors 50, 51 adapted for connection of an automated cardio pulmonary resuscitation unit. The form of connector 50, 51 is adapted to cooperate with connectors on the automated cardio pulmonary resuscitation unit.

Figure 11A:
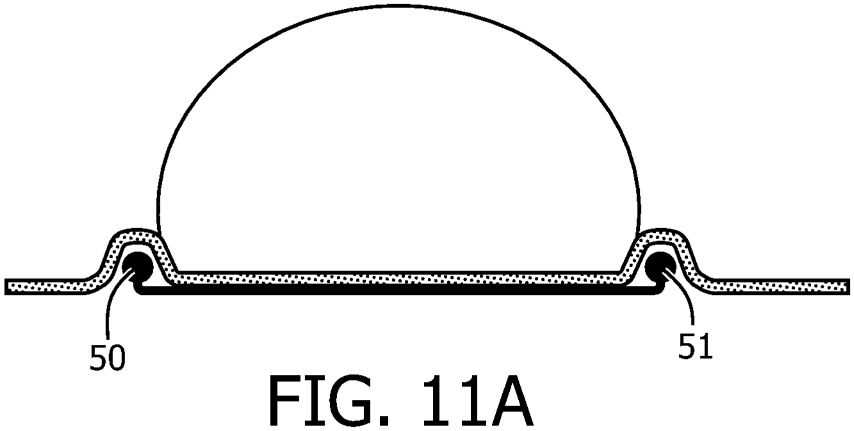
FIG. 11A, in a sectional view, shows a prior art backboard, a patient placed on the backboard, the patient having cut open clothes.
Figure 11B:
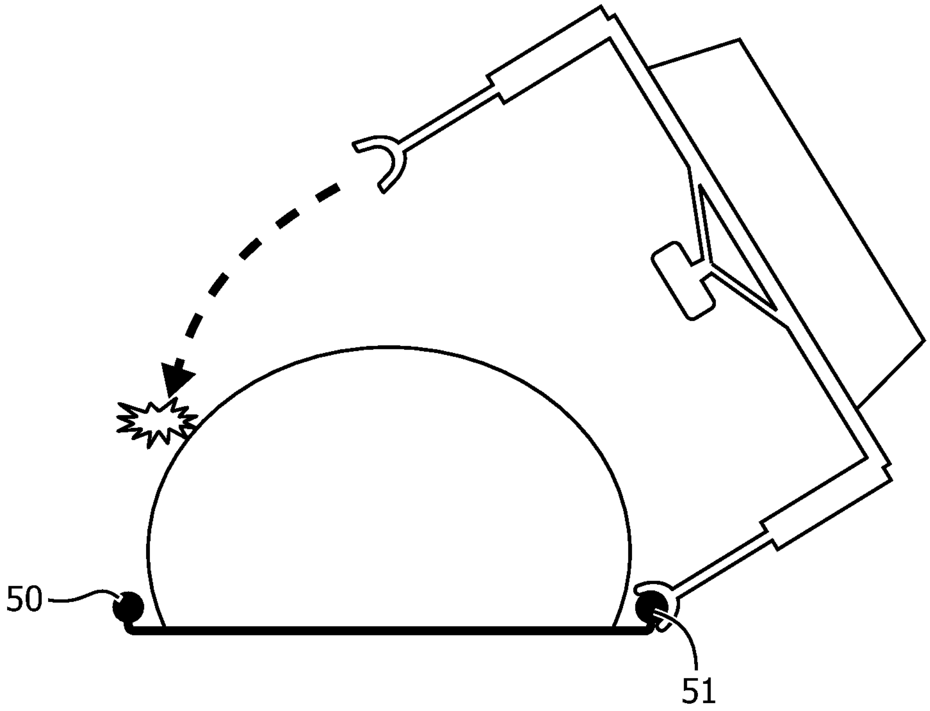
FIG. 11B, in a sectional view, shows a prior art backboard, a patient placed on the backboard during attachment of an automated cardio pulmonary resuscitation unit.

In an embodiment (not shown) the connectors 50, 51 may be provided on the side edges 13, 14 of the board element 10 for connection of an A-CPR unit, similar to the prior art devices as indicated in FIGS. 11A, 11B. The connectors may be formed in a metal material, or they may be formed in plastic, e.g. as an integrated part of the board element.

However, in preferred embodiments (see e.g. FIGS. 2-3), the board element 10 further comprises a second set of arms 60, 61 extendable from said board element 10 in a direction perpendicular to said side edges 13, 14 and in a direction perpendicular to said plane P of the board element 10. In these embodiments, the connectors 50, 51 are formed on the extendable arms 60, 61. The connectors 50, 51 may be formed of a metal material, or they may be formed of plastic. The connectors 50, 51 may be formed as an integral part of the extendable arms 60, 61.

Figure 2:
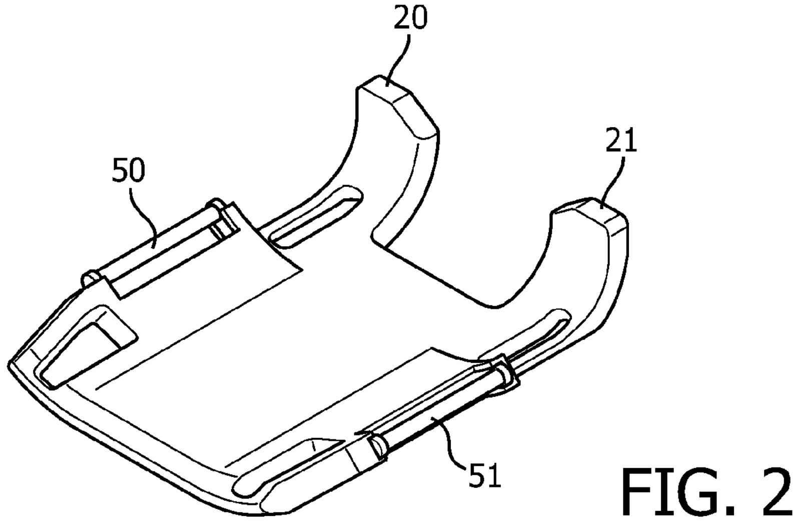
FIG. 2, in another perspective view, shows of the backboard shown in FIG. 1A, a second set of arms in an unextended position.
Figure 3:
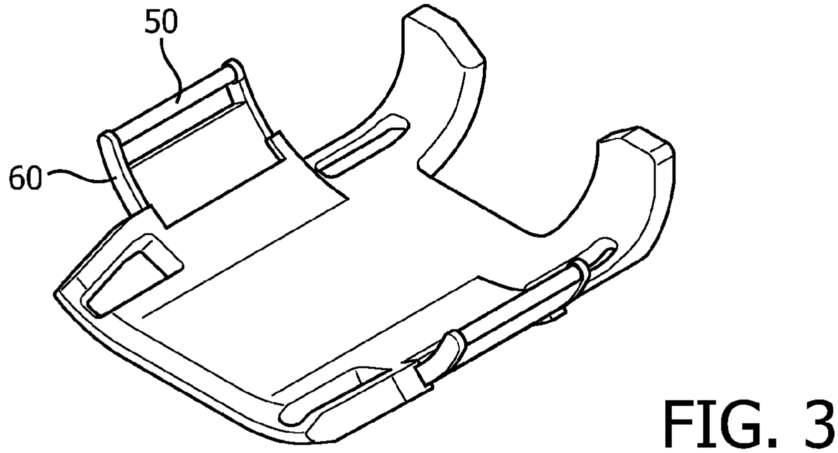
FIG. 3 shows the backboard of FIG. 2 with the second set of arms in an extended position.
Figure 4:
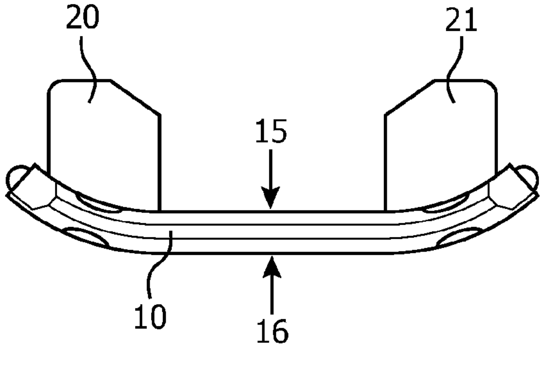
FIG. 4, in a front view, shows the backboard of FIG. 2 with the second set of arms in an unextended position.
Figure 5:
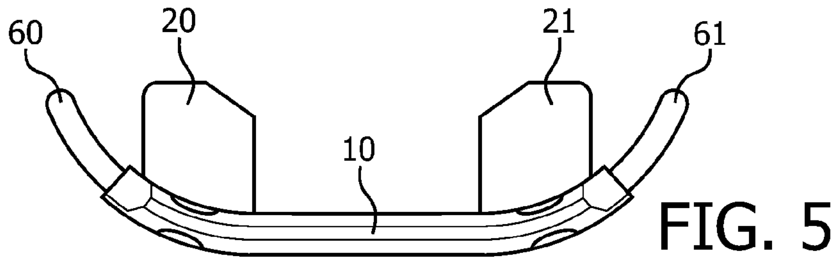
FIG. 5, in a front view, shows the backboard of FIG. 2 with the second set of arms in an extended position.
Figure 6:
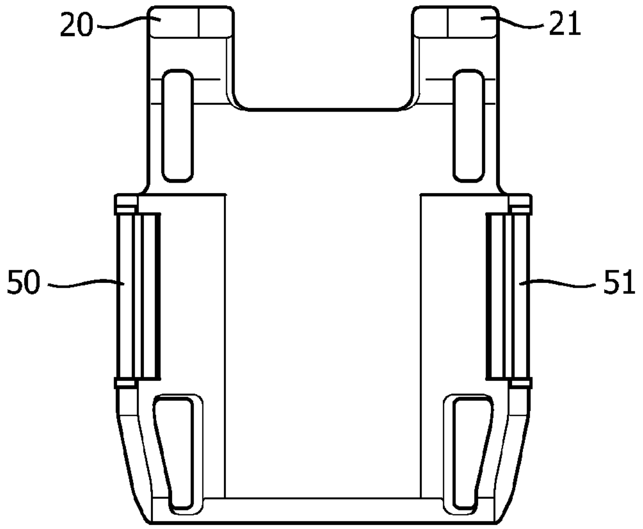
FIG. 6, in a top view shows the backboard of FIG. 2 with the second set of arms in an unextended position.
Figure 7:
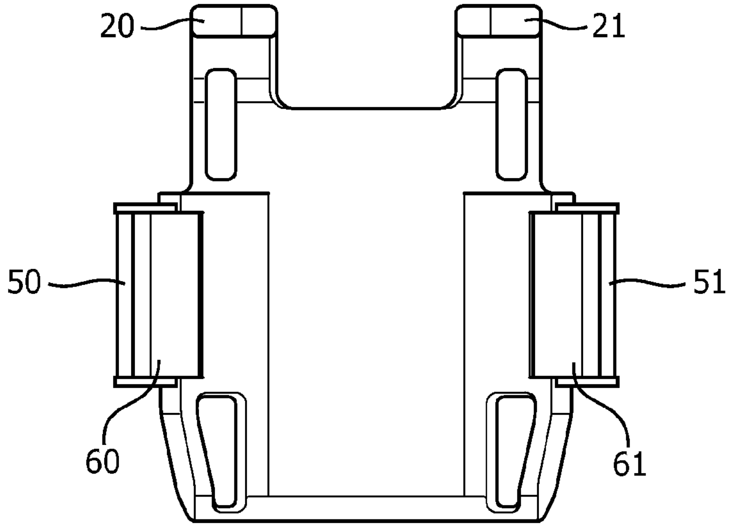
FIG. 7, in a top view, shows the backboard of FIG. 2 with the second set of arms in an extended position.

The second set of arms 60, 61 will reduce the possibility of movement of a patient in a direction perpendicular to said side edges 13, 14, and thereby serves the function of stabilizing the patient on the backboard 1. The second set of arms 60, 61 are adjustable or extendable from a closed position to an extended position. In the closed position the connectors 50, 51 formed on the arms 60, 61, respectively, are located adjacent to the surface 15 of the board 10, as shown in FIGS. 2, 4 and 6. In the extended position, the connectors 50, 51 formed on the arms 60, 61, respectively, are extended to positions over the plane P (or surface 15) and away and clear from the side edges 13, 14, as shown in FIGS. 1A-C, 3, 5, 7 and 8. In preferred embodiments, adjusting or extending of the arms is provided by a sliding mechanism that slides the arms 60, 61 in a chute or similar guiding mechanism from a closed to an extended position.

In other embodiments (not shown), adjusting or extending of the arms may however be provided by hinges that allow for rotation of the arms 60, 61 so that the arms 60, 61 can be rotated from a closed to an extended position.

A locking mechanism for locking the second set of arms 60, 61 in the extended position may be provided. Such a locking mechanism may be provided by splits and/or similar locking mechanisms.

Figure 12A:
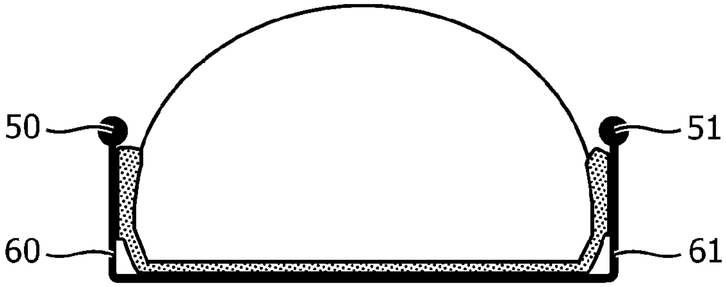
FIG. 12A, in a sectional view, shows a backboard according to an embodiment of the invention, a patient placed on the backboard, the patient having cut open clothes, and with a second set of arms in an extended position.
Figure 12B:
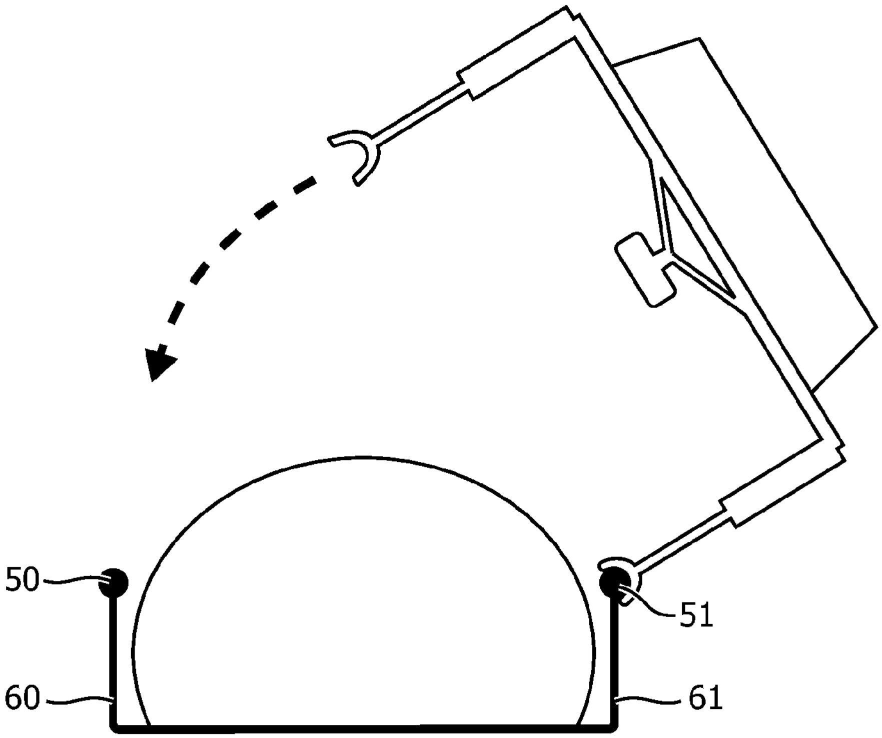
FIG. 12B, in a sectional view, shows the backboard of FIG. 12A during attachment of an automated cardio pulmonary resuscitation unit.
Figure 13:
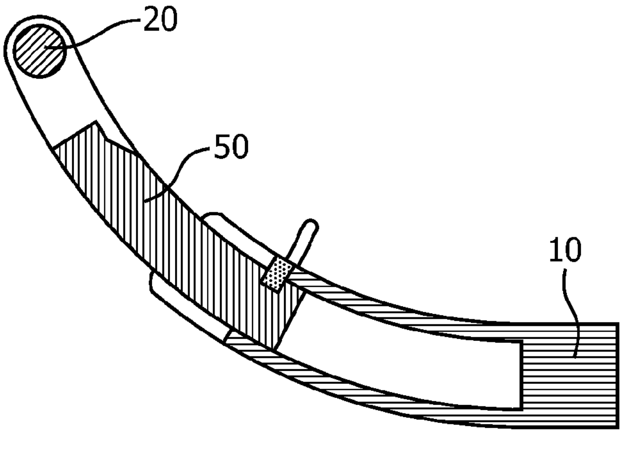
FIG. 13, in a sectional view shows one embodiment of the sliding-second arm mechanism.

The extension of the arms 60, 61, and thereby the connectors 50, 51, is further advantageous in order to prevent obstructing access to the connectors 50, 51, during use. With the prior art devices (see FIGS. 11A and 11B), where the connectors 50, 51 were located at a position at the side edges of the backboard (a position similar to the described closed position, of the second set of arms 60, 61 in the present embodiments of the invention), the patients cut open clothes would prevent access to the connectors, as shown in FIG. 11A. Further, if the patient is large, e.g. due to a trauma induced swelling or obesity, the extendable arms 60, 61 enable the second set of arms 60, 61 to slide out to an extended position thus enabling the A-CPR unit to be connectable to connectors 50, 51, without inducing damage to the patients. In FIG. 11B it is illustrated how a patient's body may obstruct the attachment of an A-CPR unit in the prior art devices. In FIG. 12B it is illustrated how the second set of arms 60, 61 may allow for easier attachment of an A-CPR unit to the connectors 50, 51.

The connectors 50, 51 are preferably formed as circular cross-section rails (see FIG. 2). In other embodiments (not shown), the connectors 50, 51 may be formed having other cross-sectional shaped rails, such as square or triangular. Thereby, the connectors 50, 51 will provide a possibility to align the A-CPR unit in a direction parallel to the side edges 13, 14 in a fast and easy way by sliding the A-CPR unit and clamping it to the connectors 50, 51 in a desired position relative to the patient and the backboard, depending on the size and shape of the patient.

In a further embodiment (not shown), the arms may be detachable from the board element 10. Thereby, the second set of arms 60, 61 may be removed, and the board element 10 and the arms 60, 61 may be efficiently cleaned and disinfected. This is important since during use there is a large risk that the backboard will be exposed to blood and/or other fluids.

The board element 10 may preferably be formed in a material transparent to common scanning systems, e.g. X-ray. Such a material may be a plastic and/or similar material. Thereby, a patient may be moved on the backboard 1 to a scanning system quickly and without providing unnecessary strain or risk to the patient by moving the him away from the supported position on the backboard.

Further, the shoulder stops 20, 21, and/or the neck support 22, and/or the head support 23 may be formed of a material transparent to common scanning systems, such as plastic.

Further, the backboard 1 may be formed in a lightweight material that minimizes the weight that needs to be carried by e.g. rescue personnel in addition to other equipment and/or the patient. Also, the lightweight material eases the handling of the backboard 1 by making it more maneuverable for rescue personnel of different strengths.

The backboard 1 may further comprise a set of handles located at the board element 10 at the side edges. The handles may be formed integral with the board element 10. The handles may be located on the board element 10, adjacent to the second set of arms 60, 61 opposite to the shoulder stops 20, 21. Such handles ease the handling of the backboard 1 and thereby the positioning and/or re-positioning of the patient on the backboard, and the positioning of the A-CPR unit. In other embodiments handles may be located at the bottom edge 12 (not shown) and/or the top edge 11 (not shown) and/or on the shoulder stops 20, 21 (see e.g. FIG. 1).

In further embodiments (not shown) the board element 10 could also be foldable along an axis parallel- or perpendicular to the side edges 13, 14 to ease the transportation and reduce size of the device for storage when not in use.

Figure 8:
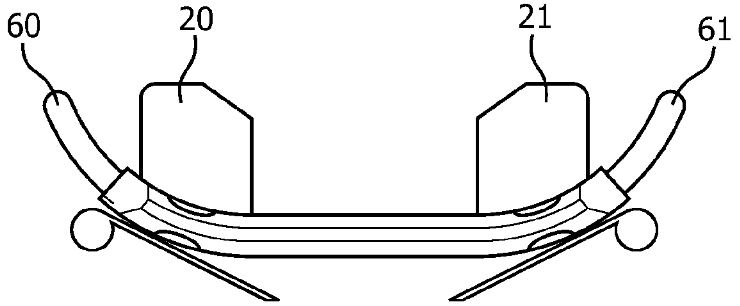
FIG. 8, in a partly sectional view, shows the backboard in FIG. 2 in use with a stretcher.

The backboard 1 may be shaped such that it suites the shape of a stretcher, as illustrated in FIG. 8, by a curving or convexity of the backside 16 of the board element 10. Thereby, rescue personnel may lift the patient onto a stretcher without removing the patient from the backboard first, and thereby keeping the patient in a supported position at all times, and saving time. Further, a curving or convexity of the backside 16 of the board element 10, may ease the process of scooping the patient onto the backboard 1.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A backboard for an automated cardio pulmonary resuscitation system, said backboard comprising:

a board element, the board element defining a plane and having a top edge, a bottom edge a first side edge and a second side edge, and providing a rest for the back of a patient;

a set of connectors adapted for connection of the backboard to an automated cardio pulmonary resuscitation unit, said connectors being provided at said side edges; and at least one set of stabilizing elements, wherein said at least one set of stabilizing element comprises a set of shoulder stops formed as rigid arms, a section of which extends away from the top edge in the plane of the board element and a section of that extends transversely to said plane, and further wherein said stabilizing elements comprises a second set of arms extendable from said board element in a direction perpendicular to said side edges and in a direction perpendicular to said plane of the board element, the connectors being located on said extendable arms.

2. A backboard according to claim 1, wherein said shoulder stops are adjustable in a direction parallel to said side edges.

3. A backboard according to claim 1, wherein said shoulder stops are adjustable in a direction perpendicular to said side edges.

4. A backboard according to claim 3, wherein said shoulder stops are L-shaped or semicircular-shaped.

5. A backboard according to claim 1, wherein said shoulder stops are formed integrated with said board element.

6. A backboard according to claim 1, wherein said second set of arms are detachable from the board element.

7. A backboard according to claim 6, wherein the second set of arms are slideably extendable from said board element.

8. A backboard according to claim 7, wherein the second set of arms is guided in guides provided in the board element from a first closed position to a second extended position.

9. A backboard according to according to claim 6, wherein the second set of arms are hingedly connected to the board element, and may be rotated to an extended position.

10. A backboard according to claim 1, wherein a set of handles are provided on said backboard.

11. A backboard according to claim 1, further comprising a set of handles disposed on the board element at the side edges adjacent to the second set of arms opposite to the shoulder stops.

12. The backboard of claim 1, further comprising: an automated cardio pulmonary resuscitation unit.

13. The backboard of claim 12, wherein said automated cardio pulmonary resuscitation unit further comprises a mechanical heart-stimulator and a respiratory aid.

* * * * *